(12) United States Patent
Devos et al.

(10) Patent No.: US 7,852,488 B2
(45) Date of Patent: Dec. 14, 2010

(54) METHOD AND DEVICE FOR CHARACTERISING A STRUCTURE BY WAVELENGTH EFFECT IN A PHOTOACOUSTIC SYSTEM

(75) Inventors: Arnaud Devos, Ennetières-en-Weppes (FR); Grégory Caruyer, Goncelin (FR)

(73) Assignee: Centre National de la Recherche Scientifique-CNRS-, Paris Cedex (FR)

( * ) Notice: Subject to any disclaimer, the term of this patent is extended or adjusted under 35 U.S.C. 154(b) by 372 days.

(21) Appl. No.: 11/922,536

(22) PCT Filed: Jun. 19, 2006

(86) PCT No.: PCT/FR2006/001386

§ 371 (c)(1),
(2), (4) Date: Dec. 19, 2007

(87) PCT Pub. No.: WO2006/136690

PCT Pub. Date: Dec. 28, 2006

(65) Prior Publication Data

US 2008/0315131 A1    Dec. 25, 2008

(30) Foreign Application Priority Data

Jun. 20, 2005   (FR) .................................. 05 51673

(51) Int. Cl.
*G01B 11/02* (2006.01)
*G01B 11/28* (2006.01)
(52) U.S. Cl. ..................... 356/503; 356/630
(58) Field of Classification Search ................ 356/503, 356/504, 630, 632
See application file for complete search history.

(56) References Cited

U.S. PATENT DOCUMENTS 4,710,030 A    12/1987   Tauc et al.

(Continued)

FOREIGN PATENT DOCUMENTS

WO    WO 2007/145702    12/2007

(Continued)

OTHER PUBLICATIONS

A. Devos: 'Giant oscillations in the picosecond ultrasonics response of crystalline silicon: Connection with the electronic structure' World Congress on Ultrasonics, 2003, pp. 1197-1200, XP002385317.

(Continued)

*Primary Examiner*—Patrick J Connolly
(74) *Attorney, Agent, or Firm*—Harness, Dickey & Pierce, P.L.C.

(57) ABSTRACT

The invention relates to a structure characterising device comprising means which are used for generating a first pump radiation and a second probe radiation and for transmitting different wavelength radiation, means for producing a time offset between said first pump and second probe radiation on the structure by means of detecting means of said second beam after the reflection or transmission thereof to said structure in such a way that an analysis signal is generated, means for processing said signal and identifying an area corresponding to the signal jump, for determining the jump amplitude according to different wavelengths, for comparing said amplitude with a theoretical amplitude variation pattern according to the wavelengths and for determining, for the wavelength characteristic for said theoretical pattern, a characteristic value associated to the structure thickness and to the radiation propagation velocity in said structure.

8 Claims, 7 Drawing Sheets

U.S. PATENT DOCUMENTS

| | | | |
|---|---|---|---|
| 5,748,318 A | | 5/1998 | Maris et al. |
| 6,108,087 A * | | 8/2000 | Nikoonahad et al. ........ 356/503 |
| 6,504,618 B2 * | | 1/2003 | Morath et al. ............... 356/630 |
| 6,552,803 B1 * | | 4/2003 | Wang et al. .................. 356/503 |
| 6,795,777 B1 | | 9/2004 | Scully et al. |
| 7,019,845 B1 * | | 3/2006 | Leary et al. .................. 356/504 |
| 7,105,811 B2 | | 9/2006 | Dantus et al. |
| 7,372,584 B2 * | | 5/2008 | Wolf ........................... 356/630 |
| 7,439,497 B2 | | 10/2008 | Dantus et al. |
| 2002/0135784 A1 * | | 9/2002 | Morath et al. ............... 356/630 |
| 2003/0099264 A1 | | 5/2003 | Dantus et al. |
| 2004/0128081 A1 | | 7/2004 | Rabitz et al. |
| 2004/0174538 A1 | | 9/2004 | Opsal et al. |
| 2004/0233944 A1 | | 11/2004 | Dantus et al. |
| 2005/0021243 A1 | | 1/2005 | Dantus et al. |
| 2006/0056468 A1 | | 3/2006 | Dantus et al. |
| 2006/0187974 A1 | | 8/2006 | Dantus |
| 2008/0170218 A1 | | 7/2008 | Dantus et al. |
| 2008/0315131 A1 * | | 12/2008 | Devos et al. ............. 250/503.1 |
| 2010/0195092 A1 * | | 8/2010 | Ohtake ........................ 356/51 |

FOREIGN PATENT DOCUMENTS

| | | |
|---|---|---|
| WO | WO 2008/011059 | 1/2008 |
| WO | WO 2008/063602 | 5/2008 |

OTHER PUBLICATIONS

D. Lim: 'Coherent optical and acoustic phonon generation correlated with the charge-ordering phase transition in La1-xCaxMn03' Physics Review Letters, vol. 86, No. 12, Apr. 2005, pp. 2669-2672, XP002385318, pp. 134403-2.

R. Cote & A. Devos: Strong picosecond ultrasonic responses of semiconductors probed close to interband transitions; Physica Status Solidi, vol. 1, No. 11, 2004, pp. 2741-2744, XP002385319, figure 2.

Oron, Dan et al.; "Quantum Control of Coherent Anti-Stokes Raman Processes;" Physical Review A, vol. 65, No. 4, XP-002386695, Apr. 2002; pp. 043408-1-043408-4.

Bartels, R.A. et al.; "Nonresonant Control of Multimode Molecular Wave Packets at Room Temperature;" Physical Review Letters, vol. 88, No. 3, XP-002386694, Jan. 21, 2002; pp. 033001-1-033001-4.

Weiner, A.M. et al.; "Generation of Terahertz-Rate Trains of Femtosecond Pulses by Phase-Only Filtering;" Optics Letters, vol. 15, No. 1, XP-000095196, Jan. 1,1990; pp. 51-53.

Cruz, J.M.D. et al.; "Use of Coherent Control Methods Through Scattering Biological Tissue to Achieve Functional Imaging;" Proceedings of the National Academy of Sciences of USA, vol. 101, No. 49, XP-002386696, Dec. 7, 2004; pp. 16996-17001.

* cited by examiner

METHOD AND DEVICE FOR CHARACTERISING A STRUCTURE BY WAVELENGTH EFFECT IN A PHOTOACOUSTIC SYSTEM

CROSS REFERENCE TO RELATED APPLICATIONS

This application is a National Stage of PCT/FR2006/001386, filed Jun. 19, 2006, which claims priority to French Application No. 0551673, filed Jun. 20, 2005, both of which are incorporated by reference herein.

BACKGROUND AND SUMMARY

The present invention relates to the field of methods of measuring the properties of structures. The present invention relates more particularly to a method of characterizing a structure by means of an acoustic wave generated and detected by light pulse. The method uses measurement of the various reflections and propagations of the wave in the structure.

In the prior art, known U.S. Pat. No. 5,748,318 describes a system for the characterization of thin films and interfaces between thin films through measurements of their mechanical and thermal properties. In the system described, light is absorbed in a thin film or in a structure made up of several thin films, and the change in optical transmission or reflection is measured and analyzed. The change in transmission or reflection is used to supply information on the ultrasonic waves generated in the structure. In that way, it is possible to determine the thicknesses of the layers and various optical properties of the structure.

The above-mentioned patent is an example of implementation of a pump-probe system that is known to the person skilled in the art and that is described generally with reference to FIG. 1, which shows an example of a known device. In this figure, the light source is a short-pulse (e.g. femtosecond) laser emitting a wave of fixed wavelength generating a first beam that is split by a beam splitter into a "pump" beam and a "probe" beam. The optical path length of the "probe" beam is then caused to vary by means of a mirror that is position servo-controlled. It is then known that the properties of the structure under the effect of the emitted beams cause a change in the reflection (or transmission) properties of the probe wave. In particular, as shown in FIG. 2, also in a manner known per se, on a graph giving change in reflection as a function of time, it is possible to observe echoes characteristic of the interfaces of a structure. Analysis of the echo signal then makes it possible to deduce, for example, the thickness of the material, if the speed of propagation of the sound wave in the medium is known. However, using that method, it is not possible to determine both the speed of propagation and the thickness of the structure.

In order to increase the number of extracted characteristics, and in particular both the speed and the thickness, the publication entitled "Evidence of Laser-Wavelength Effect in Picosecond Ultrasonics: Possible Connection with Interband Transition" (Physics Review Letters, Mar. 12, 2001, Volume 86, Issue 12) describes the use of a pump-probe device as described above, but associated with a wavelength-tunable laser, thereby making it possible to cause the wavelength of the emitted signals to vary. By means of such wavelength effects, it is then possible to determine both thickness characteristics and speed characteristics for certain types of structure. As described in the publication entitled "A Novel Approach Using Picosecond Ultrasonics at Variable Laser-Wavelength for the Characterization of Aluminium Nitride Films Used for Microsystem Applications" (A. Devos, G. Caruyer, C. Zinck, and P. Ancey), World Congress on Ultrasonics (Paris Sep. 7-10, 2003), pp. 793-796 ISBN 2-9521105-0-6), for a structure that is transparent to the probe beam, an acousto-optical interaction appears in the material that causes oscillations to appear instead of mere pulses observed by echo. Such oscillations, referred to as "Brillouin" oscillations have a period dependent on the wavelength of the probe and on the speed of sound in the material. They are shown in FIG. 3 for two samples of SiN/Al/Si and $SiO_2$/Al/Si. In that example, it can be understood that the materials and the thicknesses distinguish the two samples from each other so that the Brillouin oscillations do not have the same period at the same wavelength for the probe signal (430 nm). The person skilled in the art can understood that measuring the period of the Brillouin oscillations gives information on the speed of sound in the material, independently of the thickness of the layer. When the acoustic wave reaches the free surface, it reflects off it by changing the sign of the deformation. This results in a jump in reflectivity appearing. The acoustic wave generated in depth by the "pump" beam carries a minute change in the thickness of the layer whose sign changes on reflection. This change is detected optically because the transparent layer then acts as a Fabry-Perot interferometer, as shown in the publication entitled "Ultrafast Vibration and Laser Acoustics in Thin Transparent Films", O. B. Wright and T. L Hyoguchi, Optics Letters, Vol. 16, page 1529 (1991).

Such jumps in reflectivity are shown in FIG. 3. It should be noted that the Brillouin oscillations can extend on either side of the jump in reflectivity. The person skilled in the art can then understand that measuring the appearance time of a jump gives information on the thickness of the material, while measuring the period of said oscillations gives information on the speed of propagation. For a material like AlN, thickness error rates of about 6% have been shown, by using the period of the oscillations and the position of an acoustic echo.

An object of the present invention is to reduce further the error rate on the measured data, while keeping the possibility of determining both thickness and speed values. The present invention thus intends to solve those prior art drawbacks by using, in particular, wavelength effects, e.g. by means of a tunable laser. To this end, the present invention is of the type described above and it is remarkable, in its broadest acceptation, in that it provides a device for characterizing a structure, said device comprising radiation generator means for generating a pump first radiation and a probe second radiation, said radiation generator means for generating said first and second radiations being suitable for delivering radiations at different wavelengths, time-shift generator means for generating a time shift between said probe second radiation and said pump first radiation at said structure, detector means for detecting said second beam after reflection off or transmission through said structure so as to generate a signal to be analyzed, and processor means for processing said signal, said device being characterized in that said processor means are suitable for identifying a zone corresponding to a jump in said signal, for determining the amplitude of said jump as a function of said different wavelengths, for comparing said amplitude with a theoretical model for variation of the amplitude as a function of wavelength, and for determining, for a wavelength that is characteristic of said theoretical model, a characterization value associated with the thickness of said structure and with the speed of propagation of radiation in said structure.

In an embodiment, in order to obtain a source whose wavelength can vary, at least one tunable laser source is used. In particular, it is possible to use two tunable laser sources, or indeed one fixed source and one tunable source. In another embodiment, the variation in wavelength is obtained by emitter means for emitting a continuum of light.

In order to make it possible to observe reflectivity jumps in accordance with the invention, said probe second radiation is chose to be suitable for interacting with at least two interfaces of layers of said structure. In order to ensure that the light signals are transmitted over a plurality of wavelengths, the device of the invention preferably further comprises a set of optical means adapted to transmit said radiations over a wavelength range corresponding to said different wavelengths.

The invention also provides a method of characterizing a structure, said method comprising the steps consisting in:
- applying a pump first radiation to said structure;
- applying a probe second radiation to said structure, said probe second radiation being time-shifted relative to the pump first radiation;
- detecting said second radiation after reflection or transmission at said structure and generating a signal representative of said second radiation after reflection or transmission;
- identifying an amplitude jump in said signal;
- causing the wavelength of said second radiation to vary in a manner such as to obtain a first jump profile as a function of wavelength;
- comparing said first profile with a theoretical second profile depending on wavelength, and on a function of the thickness and of the optical index of said structure; and
- deducing therefrom a value associated with the thickness and with the optical index of said structure.

For the purposes of the present Application, the term "jump" corresponds to an analysis zone presenting high variation in the mean value of reflectivity. The amplitude of a jump is then the difference in said mean values on either side of said zone. In the presence of Brillouin oscillations, the mean value is calculated over a length of time corresponding substantially to a Brillouin oscillation period.

BRIEF DESCRIPTION OF THE DRAWINGS

The invention can be better understood from the following description of an embodiment of the invention given merely by way of explanation and with reference to the accompanying figures, in which.

DETAILED DESCRIPTION

Figure 6:
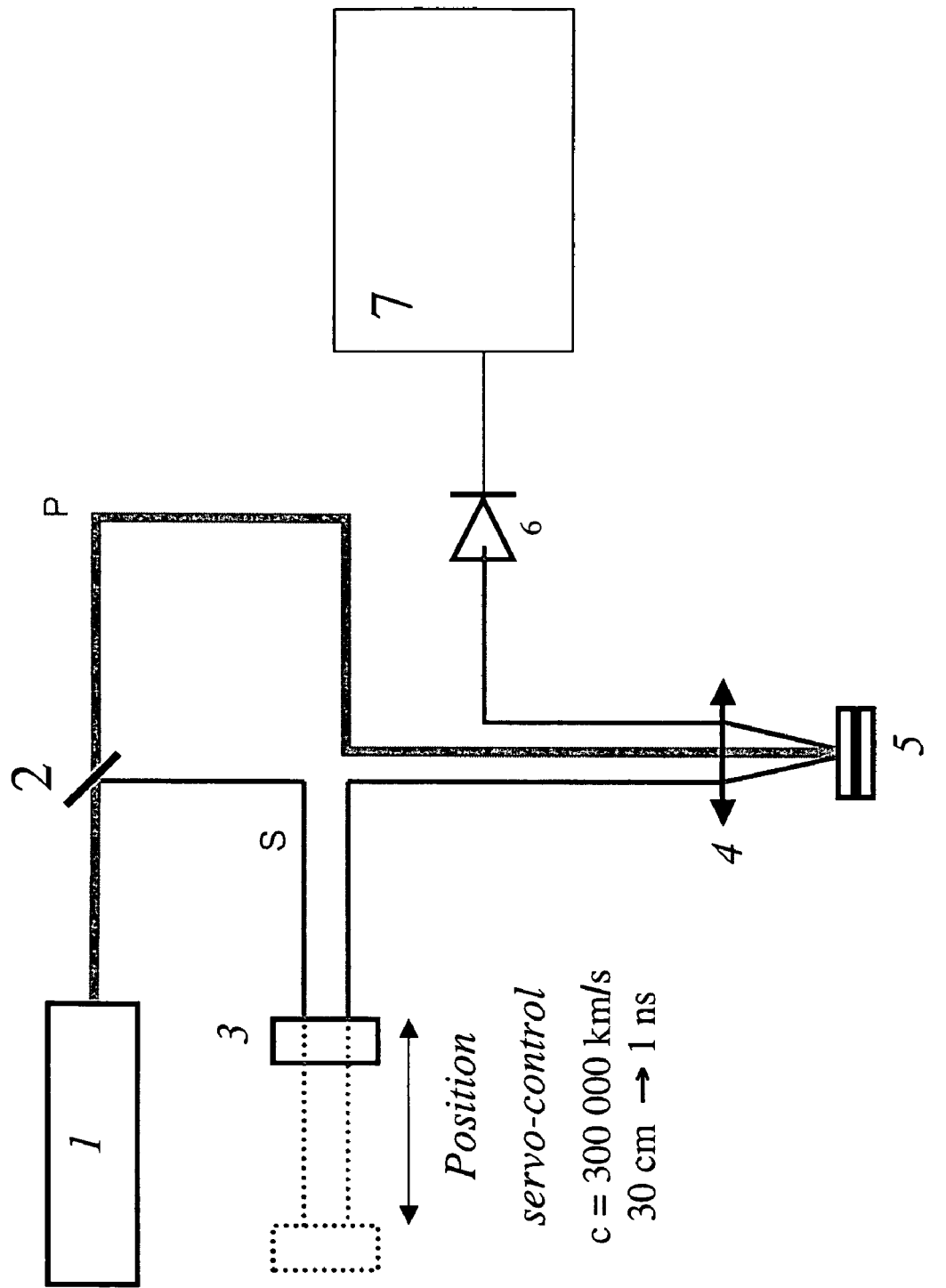
FIG. 6 shows an embodiment of the invention.

As shown in FIG. 6, the device of the invention includes a short-pulse laser source 1. The short pulses of the source must be adapted to match the desired time resolution. Pulses of about 1 ps or of about 0.1 ps are imaginable.

In a first embodiment, the source is wavelength-tunable via a tunable oscillator of the titanium-sapphire type that can generate pulses of 120 fs at a repetition rate of 76 MHz centered on a wavelength that is tunable in the range 700 nm to 990 nm. This source generates a signal that is split by a splitter 2 into a pump signal P and a probe signal S, both of which are designed to interact with the structure 5 to be analyzed. The probe signal S is subjected to a variation in optical path length relative to the pump signal P, e.g. via a moving mirror 3 that is position servo-controlled. Said probe signal is then focused on the structure 5 by an optical system 4, and is reflected towards detection means 6, e.g. of the photodetector type that are designed to generate a signal that can be analyzed by computation and processing means 7. Naturally, the probe signal can also be detected in transmission through the structure 5.

In order to enable the signals to go along the proper path from the source to the structure, the optical system is adapted to the variation in wavelength coming from the source. The person skilled in the art is capable of adapting said optical system depending on the chosen sources and wavelength ranges, and merely a few examples of usable optical systems are given herein.

The optical systems should preferably be broadband as regards both mirrors and treated lenses. In order to achieve a signal-to-noise ratio that is sufficient, pump-probe experiments use modulation of the pump beam and demodulation of the probe. The modulation should be performed outside the noise range of the laser, typically a few 100 kHz. It is performed by an acousto-optical modulator that acts as an electrically controlled grating. The diffraction of the pump beam by the grating varies with varying wavelength. Thus, by changing wavelength, the pump beam sees its direction change so that it is possible that the device might lose its setting. It is thus possible to use an acousto-optical modulator that can be controlled with an electrical signal of variable frequency. The deviation of the beam is thus compensated by changing the pitch of the grating that is generated electrically.

When a half-wavelength is used that is obtained by optical doubling in a non-linear crystal, e.g. of the Beta Barium Borate (BBO) type, the doubling is based on a phase tuning condition being satisfied in the crystal, which condition is related to its angular position relative to the beam. The change of wavelength must be made up on that angle. This is performed manually or automatically. At the outlet of the detector, the processor means 7 receiving the signal are constituted by a computer of known type that enables the processing of the invention to be implemented.

The person skilled in the art can easily understand that the pump and probe beams can also be generated by two distinct sources. In which case, the sources can themselves be moving sources in order to generate the variation in the optical path length of the probe signal relative to the pump signal. It is also possible to use a fixed-wavelength laser source, and a tunable source.

In a second embodiment, the source 1 makes it possible to generate a continuum of light extending over a wide wavelength range. In which case, the detector means 6 can comprise a spectrometer (not shown) serving to analyze the intensity of the light received before transmitting the signal to be analyzed to the processor means 7. Any system of filters in front of a usual photodetector can also be used. The plurality of wavelengths is then achieved continuously, e.g. by a fixed-wavelength femtosecond laser associated with an optical fiber.

In general, it is understood that the type of source used is not limiting to the present invention and that any type of source 1 making it possible to generate short laser pulses corresponding to a discrete or continuous set of wavelengths can be used. Similarly, in all of the embodiments, it is possible to use any means suitable for generating a time shift between the pump first beam and the probe second beam. This shift can thus be generated by varying optical path length as described above, or indeed by means making it possible to adjust the time of arrival of one pulse relative to another.

At the processor means 7, a theoretical model is stored for variation of the jump amplitude as a function of wavelength. This theoretical model is obtained from a simple physical model making it possible to understand the origin of the jumps observed in the signal as a function of wavelength.

A transparent layer of the structure 5 acts as an optical resonator of the Fabry-Perot type for the probe light. In the presence of a deformation pulse, the layer behaves as if its thickness were slightly smaller or slightly larger depending on the sign of said deformation. If a jump appears on reflection of the acoustic pulse off the free surface, it is because it becomes extensive whereas it was compressive. Since the thickness changes slightly, the reflectivity of the interferometer system constituted by the transparent layer changes accordingly.

It is possible to establish an analytical expression for the change in reflectivity induced by such a mechanism. Firstly, the reflectivity of a transparent thin layer of finite thickness e is written:

$$r = \frac{r_{01} + r_{12} e^{2ik}}{1 - r_{01} r_{12} e^{2ike}},$$

where $r_{01}$ (or $r_{12}$) designates the electromagnetic reflection coefficient between the media 0 and 1 (or 1 and 2), the subscripts 0, 1, and 2 corresponding generally to a succession of layers 0, 1, and 2.

The deformation acoustic pulse carries a very small variation in thickness of the layer (referenced $\Delta e$), which allows us to write the effect on the reflectivity $\Delta r$ in the following form:

$$\Delta r = \left(\frac{\partial r}{\partial e}\right) \Delta e$$

More precisely, the quantity obtained experimentally is the relative change of reflectivity in intensity:

$$\frac{\Delta R}{R} = 2\Re\left(\frac{\Delta r}{r}\right) = 2\Re\left(\frac{1}{r}\frac{\partial r}{\partial e}\right)\Delta e$$

Figure 5:
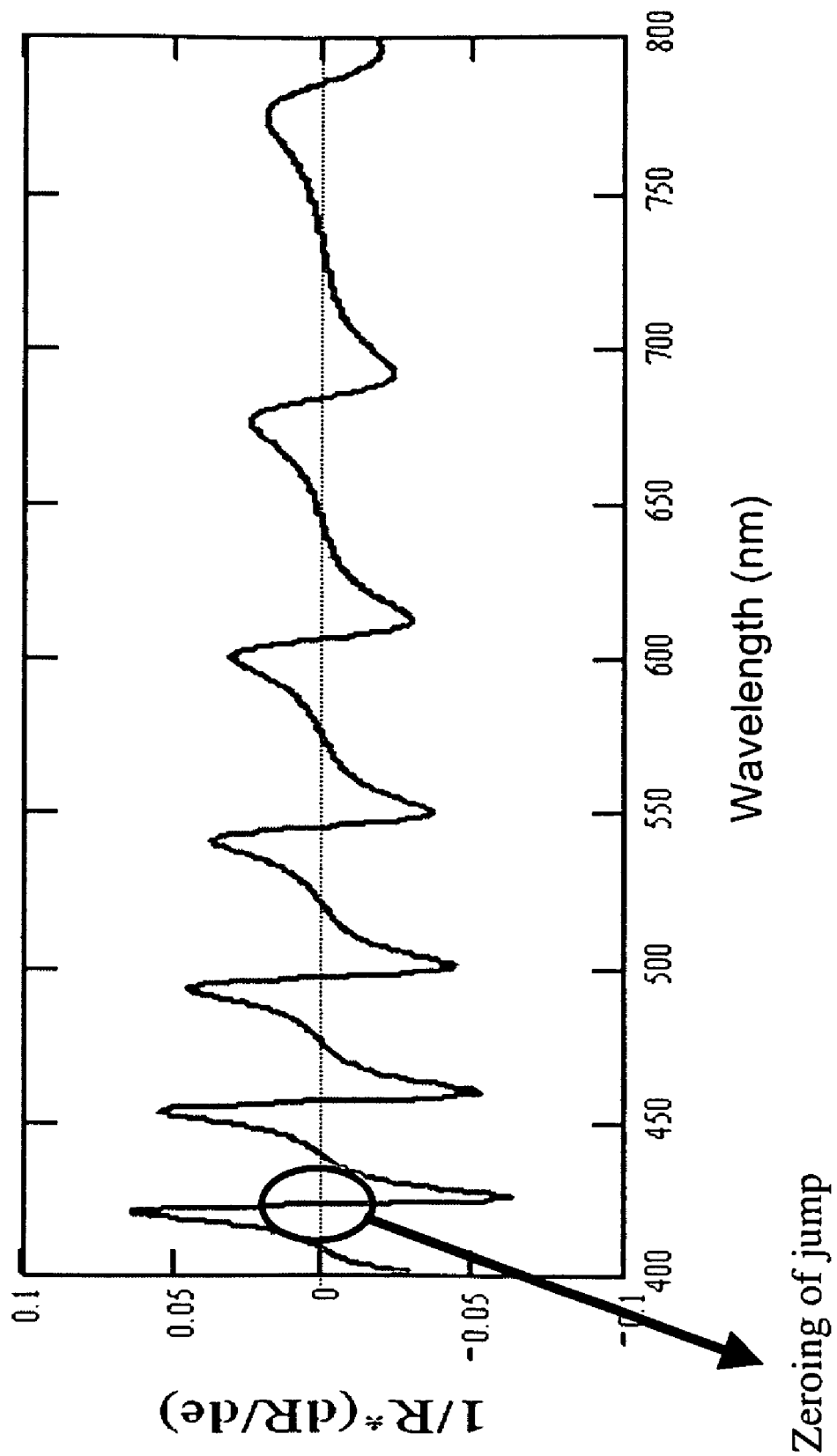
FIG. 5 shows an example of a theoretical model of how jump amplitude varies as a function of wavelength.

Thus, the physical effect that concerns us results from the derivative of the complex reflectivity of the transparent layer. On the basis of this result, we can trace the expected changes as a function of the probe wavelength as shown in FIG. 5. In particular, it can be noted that, by exploring the signs of the jumps over well-chosen wavelength ranges, it is possible to determine at least one zeroing wavelength.

Figure 1:
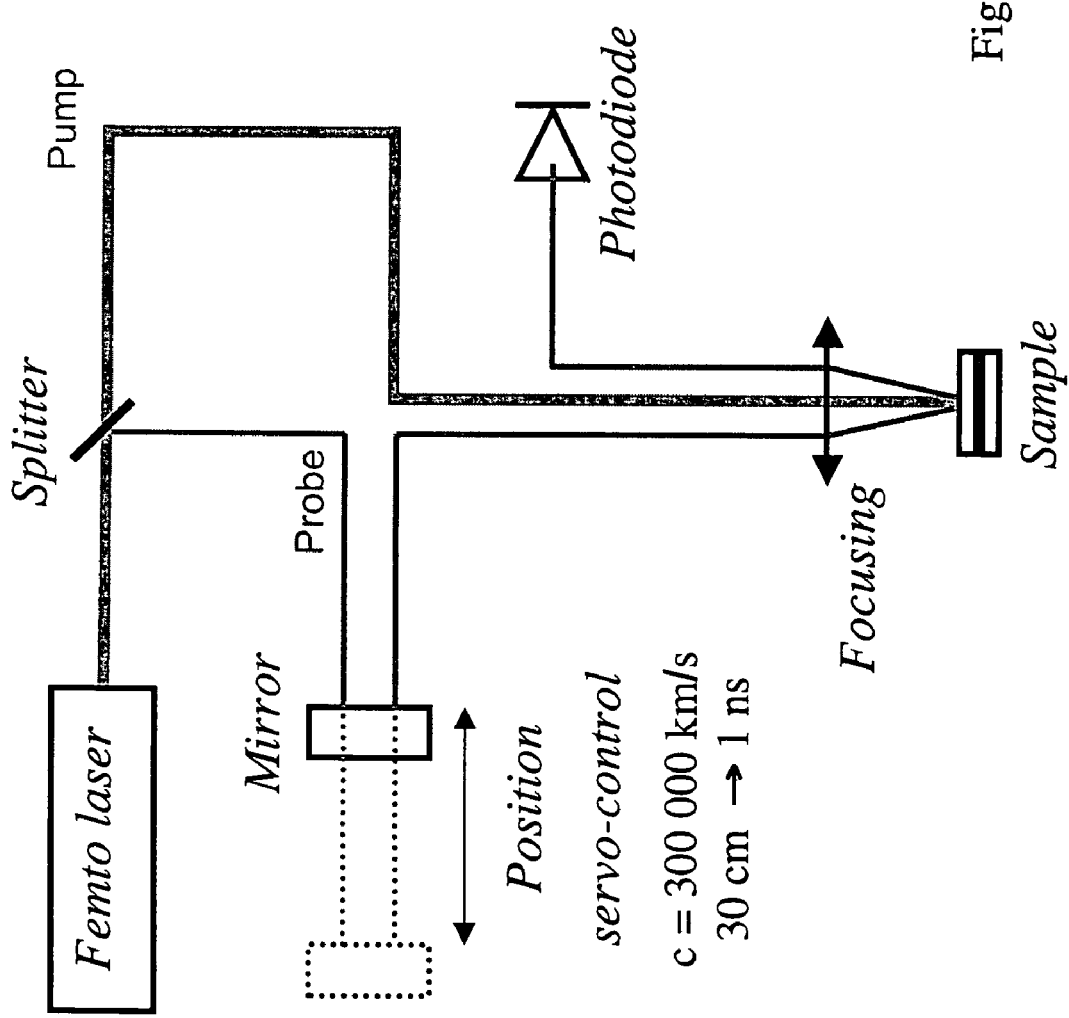
FIG. 1 is an overall view of a pump-probe device as known from the prior art.
Figure 2:
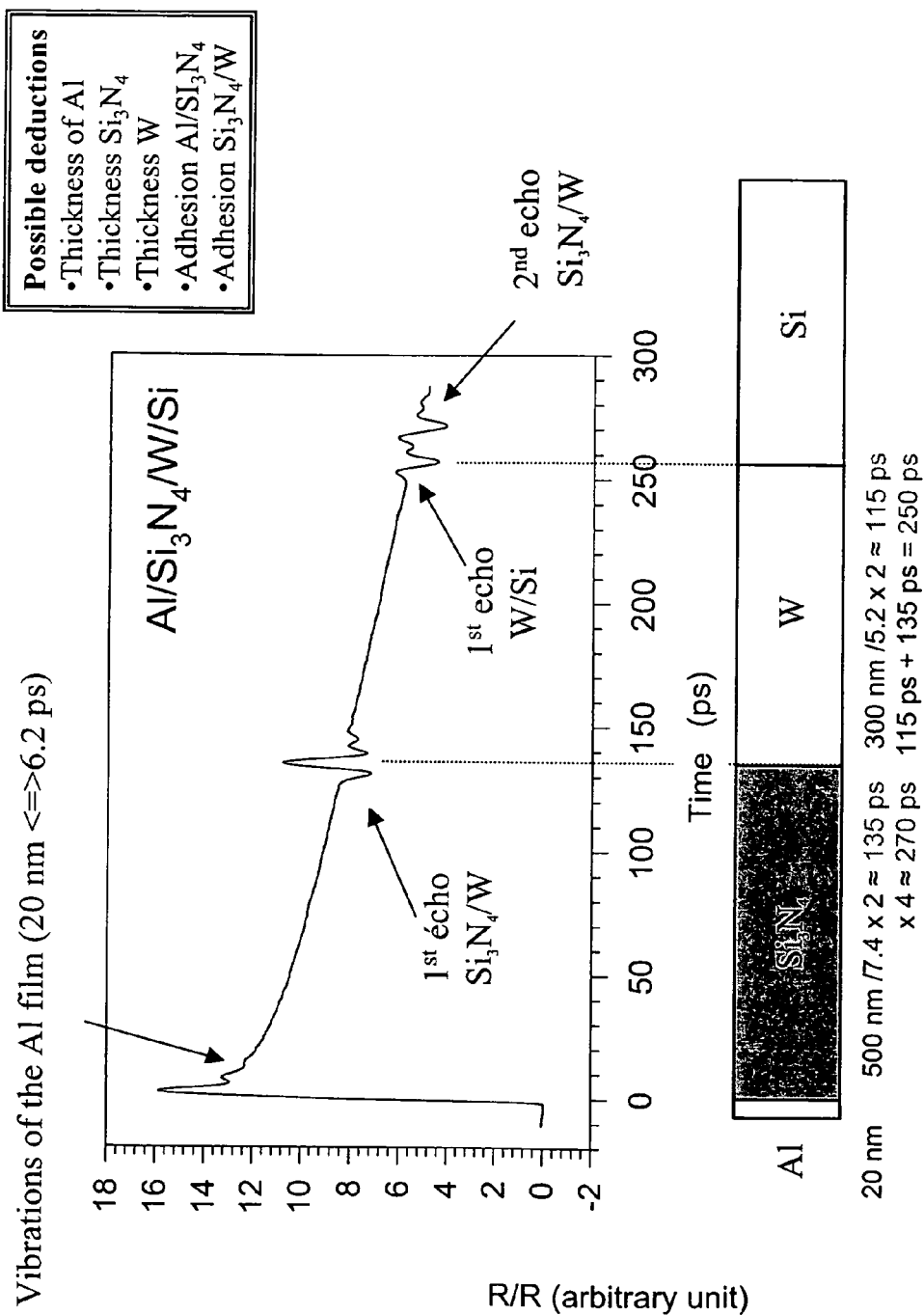
FIG. 2 shows an example of a result obtained using the pump-probe device of FIG. 1.
Figure 3:
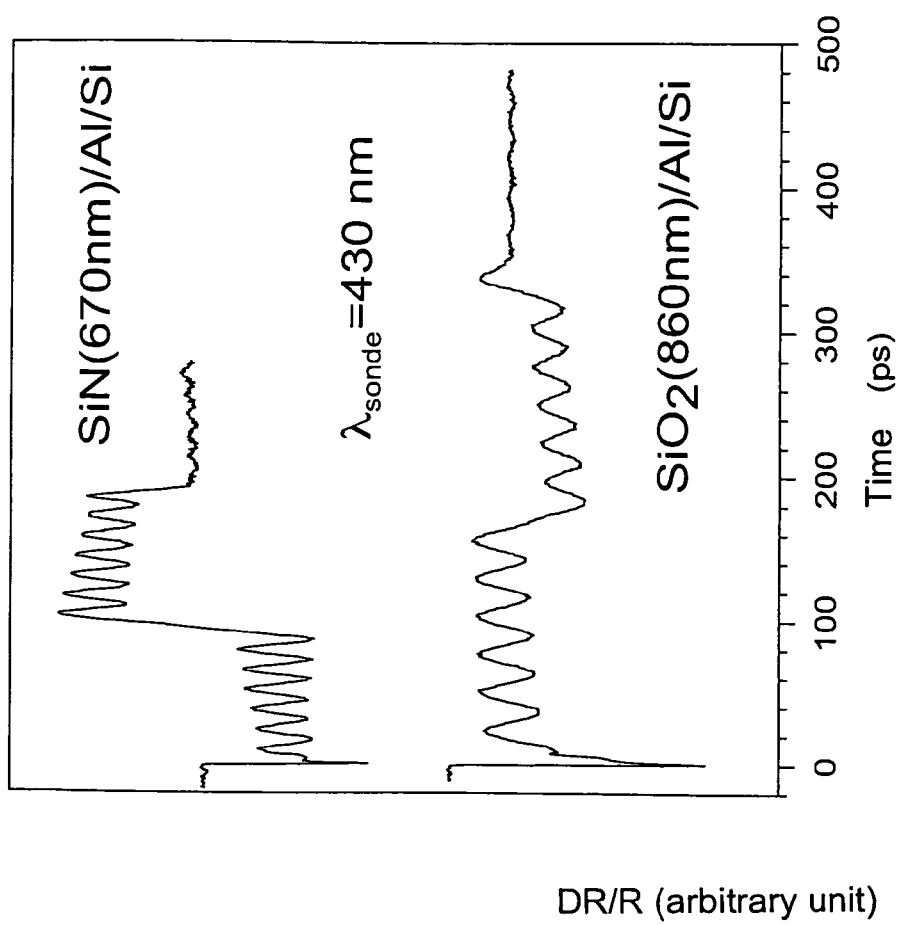
FIG. 3 shows an example of characterization by Brillouin oscillation and jump in reflectivity as known from the prior art.
Figure 4A:
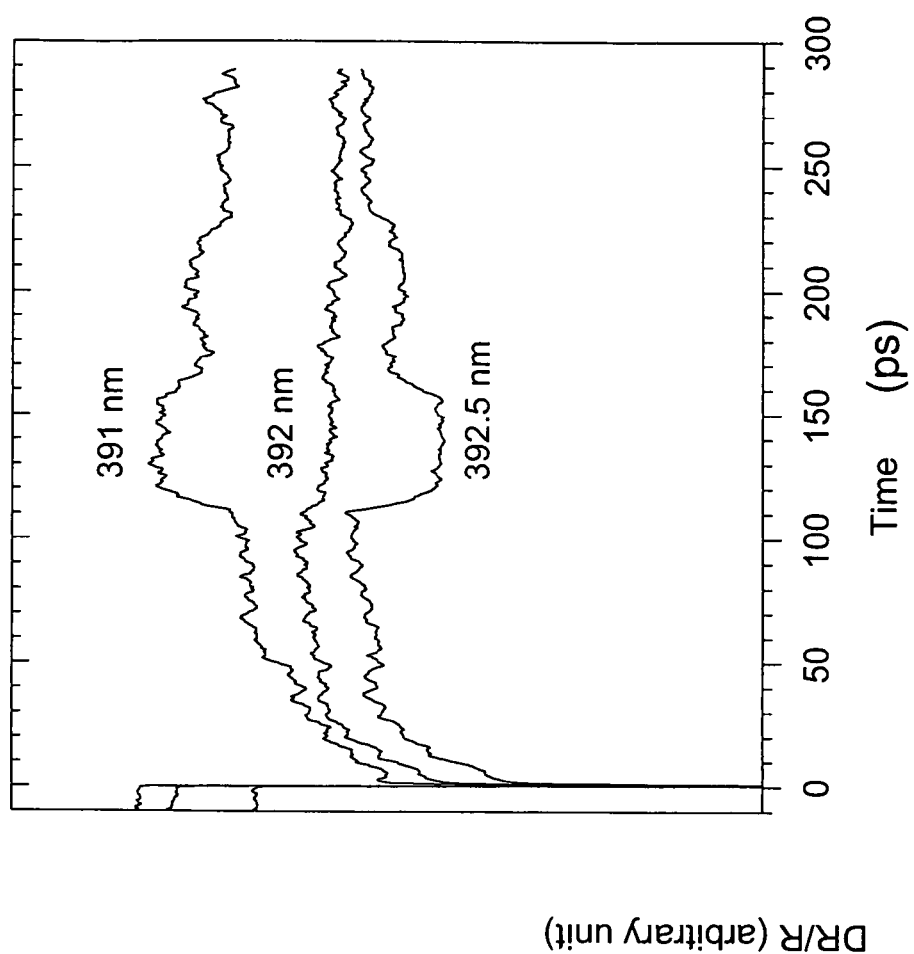
FIGS. 4a and 4b show an example of measuring jumps in reflectivity in the Brillouin oscillation zone for various wavelengths.
Figure 4B:
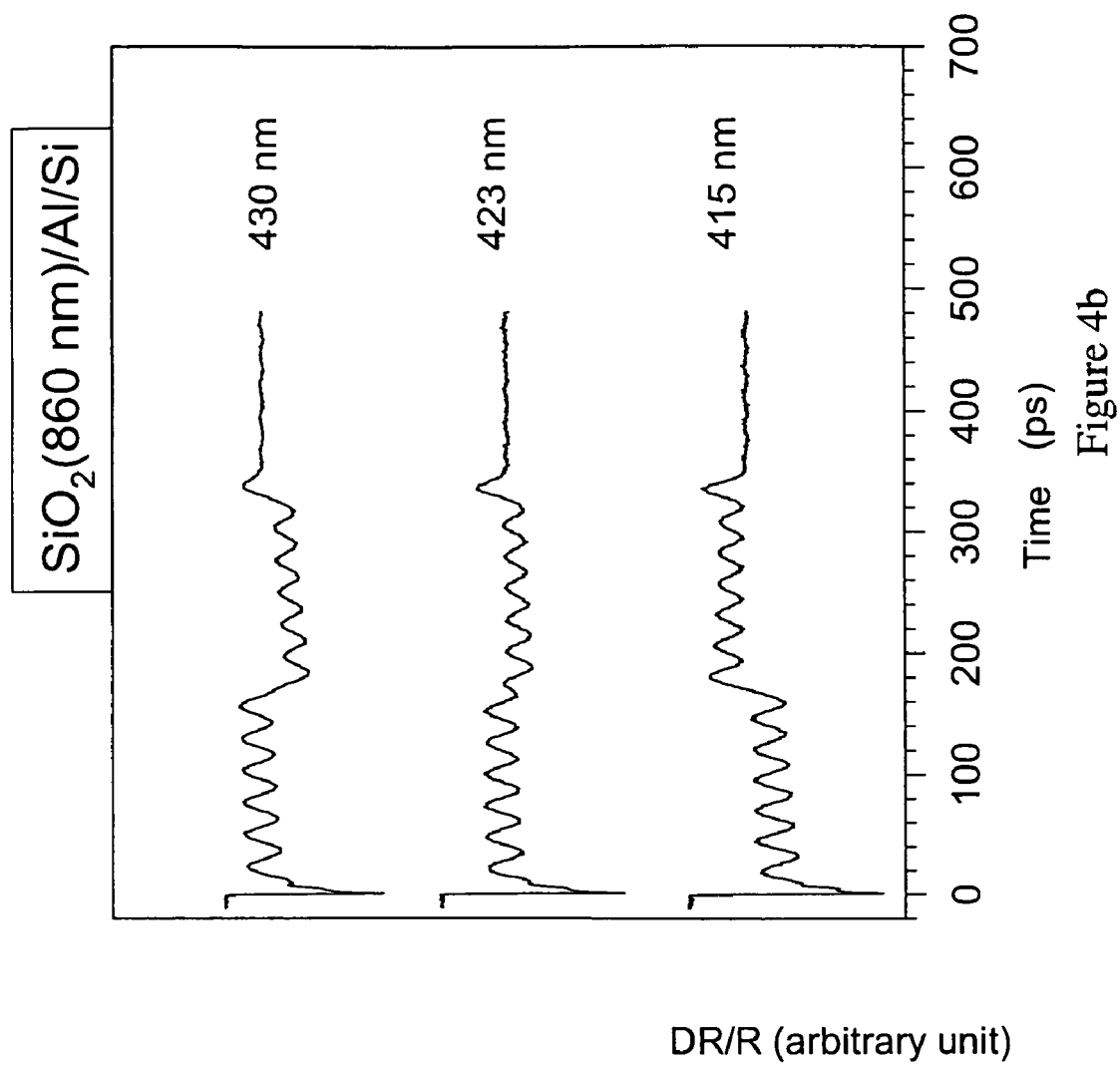

In accordance with the invention, the wavelength of the probe radiation is caused to vary and the zeros of the amplitude of the jumps in the signal are detected, as are the associated changes of signs, as shown in FIGS. 4a and 4b. It should be noted that, since the variation in the amplitude of the jumps as given in FIGS. 4a and 4b represents experimental results, said variation is very sensitive to wavelength, as confirmed by the theoretical slope at the time of zeroing in FIG. 5. In accordance with the invention, the heavy wavelength dependency can also be used to identify the reflectivity jumps more clearly. Thus, a step of identifying an amplitude jump can itself include a sub-step of varying the wavelength. Such an identification step can easily by implemented by a test as a function of a threshold of amplitude variation over a given time, optionally with the wavelength being varied. Thus, by comparing the zeros of the jumps of the signal obtained after detection with the theoretical model, it is possible to determine a wavelength $\lambda_0$ characteristic of zeroing.

However, depending on the model adopted, the relative change of reflectivity in intensity $$\frac{\Delta R}{R}$$

is a function only of the wavelength, of thickness of the transparent layer, and of the speed of propagation of the wave (or of the optical index of the layer), and more precisely, of the product of the optical index multiplied by the thickness of the layer n.e. Determining the zeroing characteristic wavelength $\lambda_0$ thus makes it possible to obtain a value characteristic of the product of the index multiplied by the thickness (n.e)$_0$. This additional information on the characteristics of the layer then makes it possible to increase considerably the precision of the results obtained.

For a Brillouin oscillation zone, the period of oscillation of the signal is measured. Using the known formula:

$$T(\lambda, n, e) = \frac{\lambda}{2nv\cos\theta}$$

it is then possible to obtain a first item of information on the index and on the thickness as a function of the wavelength. By then placing ourselves at the zeroing characteristic wavelength, the product (n.e)$_0$ is set.

It is also possible to measure the oscillation time for the Brillouin oscillations $$t(e, v) = 2 \cdot \frac{e}{v}$$

corresponding to one go-and-return of the wave in the layer, which gives a third item of information on the index and on the thickness. The person skilled in the art can then easily understand that the data constituted by the product (n.e)$_0$ of the invention considerably increases the precision of the results on the index and thickness values.

In particular, the Applicant has shown that, for a structure of the AlN/Al/Ti/Si type, e.g. in a resonator of the Bulk Acoustic Wave (BAW) type, the method of the present invention makes it possible to cause the uncertainty in thickness to go from 6% in the absence of determination of the product (n.e)$_0$ to 0.17% with such determination. It can also be noted that it is possible to refine the physical model shown in FIG. 5 by involving new effects. In particular, it is also possible to affect the reflectivity of the layer via the optical index (photoelastic effect). The reflectivity jump detected can then be written as the sum of two synchronous contributions in wavelength, i.e. the inversions and the zeroing take place simultaneously.

Furthermore, we have described an example in which the comparison with the theoretical model is made relative to a point of zeroing of the jump amplitude as a function of wavelength, but naturally any point or characteristic of the physical model can be used. It can thus be the maxima, the decreasing of the maxima, the spacing between two zeros, etc.

The present invention relates particularly but not exclusively to any transparent layer on a substrate or on an absorbent layer. More generally, the probe signal must be suitable for "seeing" the two end interfaces of any given layer. This is thus achievable on a layer that is relatively absorbent but that is fine enough for the probe signal to reach the end that is further away. Preferably, the pump signal should also be absorbed in depth into the structure.

An implementation is given for a layer of AlN in a BAW resonator, but naturally the device of the invention operates for any type of structure as defined above. The method can, for example, be used for the "loading" layer of $SiO_2$ which is deposited on the upper electrode of a component. The Applicant has also been able to characterize "high-K" thin layers of oxides of the $SrTiO_3$ and $BaTiO_3$ types by using the method and the device of the invention. The invention is described above by way of example. Naturally, the person skilled in the art is capable of implementing various variants of the invention without going beyond the ambit of the patent.

The invention claimed is:

1. A device for characterizing a structure, said device comprising:
    at least one radiation generator operably generating a pump first radiation and a probe second radiation, said radiation generator operably generating said first and second radiations being suitable for delivering radiations at different wavelengths, a time-shift generator operably generating a time shift between said probe second radiation and said pump first radiation between said radiation generator and a structure, detector operably detecting said second beam after reflection off or transmission through said structure so as to generate a signal to be analyzed, and a processor operably processing said signal;
    wherein said at least one processor operably identifies a zone corresponding to a jump in said signal, determines the amplitude of said jump as a function of said different wavelengths, compares said amplitude with a theoretical model for variation of the amplitude as a function of wavelength, and determines, for a wavelength that is characteristic of said theoretical model, a characterization value associated with the thickness of said structure and with the speed of propagation of radiation in said structure.

2. A device according to claim 1, wherein said radiation generator generates electromagnetic radiations at different wavelengths and comprises at least one tunable laser source.

3. A device according to claim 1, wherein said radiation generator generates electromagnetic radiations at different wavelengths and comprises at least one emitter operably emitting a continuum of light.

4. A device according to claim 1, wherein said probe second radiation is suitable for interacting with at least two interfaces of layers of said structure.

5. A device according to claim 1, further comprising a set of optics transmitting said radiations over a wavelength range corresponding to said different wavelengths.

6. A device according to claim 1, wherein said radiation generator generates electromagnetic radiations at different wavelengths and comprises two tunable laser sources.

7. A device according to claim 1, wherein said radiation generator generates electromagnetic radiations at different wavelengths and comprises at least one fixed laser source and one tunable laser source.

8. A method of characterizing a structure, said method comprising:
    (a) applying a pump first radiation to said structure;
    (b) applying a probe second radiation to said structure, said probe second radiation being time-shifted relative to the pump first radiation;
    (c) detecting said second radiation after reflection or transmission at said structure and generating a signal representative of said second radiation after reflection or transmission;
    (d) identifying an amplitude jump in said signal;
    (e) causing the wavelength of said second radiation to vary in a manner such as to obtain a first jump profile as a function of wavelength;
    (f) comparing said first profile with a theoretical second profile depending on wavelength, and on a function of the thickness and of the optical index of said structure; and
    (g) deducing therefrom a value associated with the thickness and with the optical index of said structure.

* * * * *